US009248027B2

(12) United States Patent
Dunworth et al.

(10) Patent No.: US 9,248,027 B2
(45) Date of Patent: Feb. 2, 2016

(54) CERVICAL IMPLANT WITH EXTERIOR FACE PLATE

(71) Applicant: SpineSmith Partners, L.P., Austin, TX (US)

(72) Inventors: Kevin Dunworth, Austin, TX (US); Richard J. Kana, Lexington, TX (US); John B. Rossman, Austin, TX (US)

(73) Assignee: SpineSmith Partners, L.P., Austin, TX (US)

( * ) Notice: Subject to any disclaimer, the term of this patent is extended or adjusted under 35 U.S.C. 154(b) by 94 days.

(21) Appl. No.: 14/055,730

(22) Filed: Oct. 16, 2013

(65) Prior Publication Data
US 2014/0046447 A1 Feb. 13, 2014

Related U.S. Application Data

(63) Continuation-in-part of application No. 14/020,374, filed on Sep. 6, 2013, and a continuation-in-part of application No. 13/135,675, filed on Jul. 12, 2011, and a continuation-in-part of application No. 13/200,911, filed on Oct. 4, 2011, now Pat. No. 8,597,353.

(60) Provisional application No. 61/714,376, filed on Oct. 16, 2012.

(51) Int. Cl.
A61F 2/44 (2006.01)
A61B 17/70 (2006.01)
A61B 17/80 (2006.01)
A61F 2/30 (2006.01)

(52) U.S. Cl.
CPC ............ A61F 2/4455 (2013.01); A61B 17/7059 (2013.01); A61B 17/8061 (2013.01); A61F 2/30744 (2013.01); A61F 2/447 (2013.01); A61F 2002/30131 (2013.01); A61F 2002/30168 (2013.01); A61F 2002/30331 (2013.01); A61F 2002/30482 (2013.01); A61F 2002/30489 (2013.01); A61F 2002/30509 (2013.01); A61F 2002/30522 (2013.01); A61F 2002/30561 (2013.01); A61F 2002/30787 (2013.01); A61F 2002/30904 (2013.01); A61F 2002/4475 (2013.01)

(58) Field of Classification Search
CPC ............ A61B 17/7059; A61B 17/8061; A61F 2002/30131; A61F 2002/30331; A61F 2002/30561; A61F 2/30744; A61F 2002/30787; A61F 2002/30904; A61F 2/4455; A61F 2/447; A61F 2002/4475
See application file for complete search history.

(56) References Cited

U.S. PATENT DOCUMENTS

| 2004/0210219 | A1* | 10/2004 | Bray | 606/69 |
| 2005/0240267 | A1* | 10/2005 | Randall et al. | 623/17.11 |
| 2007/0123989 | A1* | 5/2007 | Gfeller et al. | 623/17.16 |
| 2009/0326580 | A1* | 12/2009 | Anderson et al. | 606/246 |
| 2010/0312346 | A1* | 12/2010 | Kueenzi et al. | 623/17.16 |

FOREIGN PATENT DOCUMENTS

| EP | 1847240 A1 * | 10/2007 | A61F 2/44 |
| WO | WO 2010146398 A1 * | 12/2010 | A61F 2/34 |

* cited by examiner

Primary Examiner — Larry E Waggle, Jr.
(74) Attorney, Agent, or Firm — Winstead PC

(57) ABSTRACT

The invention is directed to a spinal fusion device, comprising a load bearing component and an anterior component, wherein the load bearing component and the anterior component are configured to mate together by complimentary coupling members, and further comprising an external outer plate configured to span two vertebrae, wherein the outer plate includes bores configured to receive bone screws for coupling to vertebrae.

4 Claims, 2 Drawing Sheets though other plate configurations are contemplated herein within the scope of the claimed invention. Furthermore, the number of anti-backout locking plates, as well as the relative size of the plates, is contemplated herein within the scope of the claimed invention. The exterior face plate 10 or anterior plate 11 is any type of plate capable of functioning within the scope of the claimed invention, including but not limited to a low profile configuration, as shown in FIG. 1.

CERVICAL IMPLANT WITH EXTERIOR FACE PLATE

CROSS-REFERENCES TO RELATED APPLICATIONS

This Application claims the benefit under 35 U.S.C. §119 (e) of U.S. Provisional Patent Application No. 61/714,376 filed Oct. 16, 2012, which is incorporated herein by reference in its entirety as if fully set forth herein. This Application is a continuation-in-part of application Ser. No. 13/135,675 filed Jul. 12, 2011, and is a continuation-in-part of application Ser. No. 13/200,911 filed Oct. 4, 2011, and is a continuation-in-part of application Ser. No. 14/020,374 filed Sep. 6, 2013, each of which is incorporated herein by reference in its entirety as if fully set forth herein.

BACKGROUND OF THE INVENTION

The spine is a series of movable segments made up of vertebrae and discs. Due to trauma, disease, and/or aging, the spine may be subject to degeneration. This degeneration may destabilize the spine and cause pain and/or nerve damage. Medical procedures are often required to either ease back pain, repair damage, or to prevent future damage.

One procedure that is often used to treat back pain or spinal damage is spinal fusion. Spinal fusion is a surgical technique used to combine two or more adjacent vertebrae. Supplemental bone tissue is used in conjunction with the patient's natural osteoblastic processes in a spinal fusion procedure. Spinal fusion is used primarily to eliminate back pain caused by the motion of the damaged vertebrae by immobilizing adjacent vertebrae. Conditions for which spinal fusion might be done include degenerative disc disease, treatment of a spinal tumor, a vertebral fracture, scoliosis, degeneration of the disc, or any other condition that causes instability of the spine.

One problem with prior art spinal fusion techniques relates to device migration. For example, prior to complete bone fusion, a fusion device may migrate from the desired position. In examples where bone screws are used, the insertion and tightening of the bone screws tends to cause device migration. Another problem with typical prior art fusion techniques is that fusion devices, or associated plates or fasteners, protrude excessively from the spine, causing discomfort, damage, or danger to surrounding vascular or neurological tissues.

Yet another problem with the prior art fusion techniques is the difficulty with placing supplemental fixation (i.e.: plates and screws) due to gross anatomy constraints, surgical approach, vasculature and neurologic tissues and structures, and variable bone quality of the vertebrae.

There is therefore a need for spinal fusion devices and related spinal fusion procedures that adequately treats degenerative disc disease and other spinal conditions.

SUMMARY OF THE INVENTION

The claimed invention, in one aspect, is a spinal fusion device, comprising: (A) a U-shaped load bearing component and an anterior component, wherein the load bearing component and the anterior component are configured to mate together, wherein the anterior component includes a middle bore that transverses the anterior face of the anterior component and the opposing face of the anterior face and (B) an external outer plate configured to span two vertebrae, wherein the outer plate a plurality of bores configured to receive bone screws for coupling to adjacent vertebrae, and wherein the outer plate includes a middle bore that aligns during use with the bore of the anterior component to receive an elongate fastener; and wherein the outer plate has a low profile.

DETAILED DESCRIPTION OF EXEMPLARY EMBODIMENTS

A typical technique for cervical disk fusion is for the surgeon to build a construct of the following components:

A spacer/cage, which is used to restore and maintain the appropriate space between vertebral bodies, and to serve as a holder for bone graft material.

An anterior plate along with several bone screws, which is used to stabilize, immobilize, and provide temporary fixation, until permanent fusion occurs.

In cases of extreme instability and/or possible trauma, the surgeon will often use posterior fixation, possibly in the form of rods and pedicle screws, to supplement the anterior plate fixation.

Without actually performing both posterior and anterior fixation, it is desired to create a device and/or method that would achieve equivalent results with only anterior fixation. A secondary problem solved by embodiments of the claimed invention involves the ability to easily position the anterior plate relative to the centerline of the spine and its alignment to the spacer/cage. Surgeons want to see post-surgical x-rays that have an appealing visual quality to them. This is particularly important to the surgeon when reviewing the x-rays with the patient.

The claimed invention eliminates the need for the supplementary posterior procedure while achieving the strength of both anterior and posterior fixation. The obvious advantages are: less time for the patient, hospital staff, and the surgeon to be in the operating room. There is no requirement for the posterior procedure, therefore the morbidity is far less which will reduces the recovery time for the patient. The risk of post-operative infection is reduced by at least 50% and overall cost will be greatly reduced.

The secondary advantage of the claimed invention is experienced with the way it easily aligns and establishes centerline relative to the spacer/cage. Additionally, the claimed device also aligns itself perpendicular to the spine centerline, therefore postoperative x-rays will be visually appealing.

This invention is intended to be used with an anterior cervical device. Particular design features are tailored towards the anterior cervical device, but the concept can be used or modified for use with other cervical devices.

Figure 1:
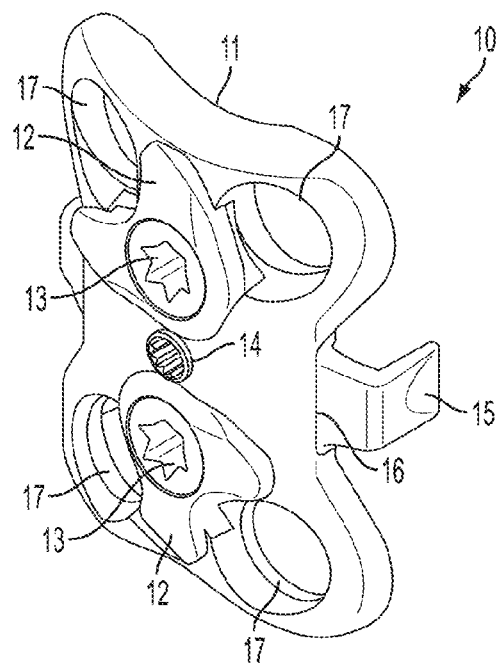
FIG. 1 shows an exterior face plate device in accordance with an embodiment of the invention.

An embodiment of the claimed invention is directed to an exterior face plate that is capable of coupling with an anterior cervical device construct to align with the center of the construct and positioned perpendicular to the construct. Referring to the accompanying drawings, as set forth in FIG. 1, an exterior face plate 10 in accordance with an embodiment of the invention is shown. As seen in FIG. 1, the exterior face plate comprises an anterior plate 11. The exterior face plate further comprises at least two anti-backout locking plates 12, each of which contains an anti-backout locking plate screw. The purpose of the anti-backout locking plate 12 and screw 13, is to prevent the bone screws that attach the exterior face plate to the anterior cervical device from backing out and/or away from the anterior plate.

The exterior face plate 10 further comprises a threaded connector 14. In certain embodiments of the invention, the threaded connector can be replaced with a ratcheting mechanism, cam connector or other connection means. The exterior face plate 10 comprises at least two alignment tabs 15. The alignment tabs 15 are located on either side of the exterior face plate 10. In certain embodiments of the invention and as shown in FIG. 1, the alignment tabs 15 are L-shaped. The alignment tabs each comprise at least one alignment tab break-away feature 16 that is located at the junction of the anterior plate 11 and alignment tab 15.

The anterior plate 11 of the exterior face plate 10 further comprises a plurality of openings 17 that are configured to receive bone screws. In certain embodiments of the invention, the anterior plate 11 comprises at least four (4) openings 17 that are positioned at the corners of the anterior plate 11, as set forth in FIG. 1.

Figure 2:
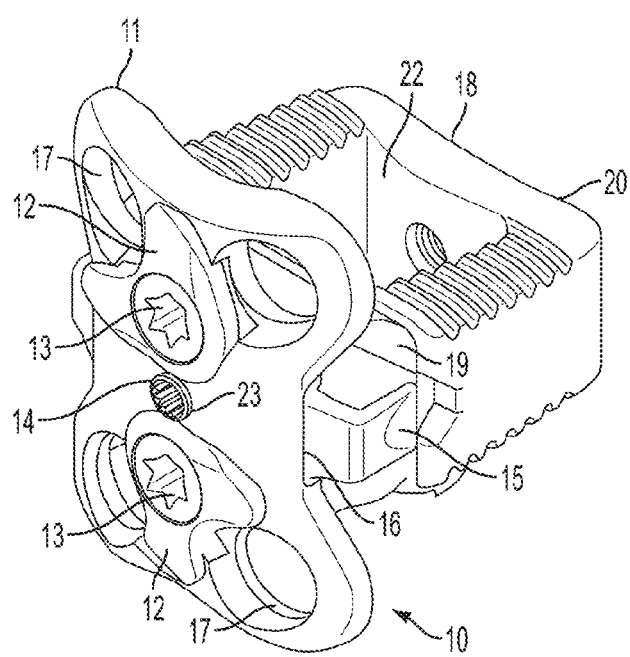
FIG. 2 shows an exterior face plate device connected to an anterior cervical device in accordance with an embodiment of the invention.

Referring now to FIG. 2, the anterior cervical device of the claimed invention 20 consists of a "U" shaped spacer/cage 18 that can be filled with graft material (not shown). A face plate 19 accompanies the cage 18. The face plate 19 mates with the cage component 18 to form an opening 22 that can be filled with graft material. The face plate 19 serves at least two purposes in the context of the anterior cervical device 20. The first purpose is to close off the cage 18 and hold the graft material in place. The second purpose is to provide a housing for the bone screws. These bone screws are driven into the vertebral bodies and provide the stability and temporary fixation of a traditional cage/spacer and anterior plate construct.

Referring now to FIG. 3, at least four bone screws 21 are able to be placed through the anterior plate 11, going into the face of the vertebral bodies 50 and 52. In addition to alignment, the anterior plate may be mechanically connected to the anterior cervical device. The combination of the anterior cervical construct and the addition of the claimed anterior plate device results in the equivalent strength and stability of an anterior/posterior fixation procedure.

Figure 3A:
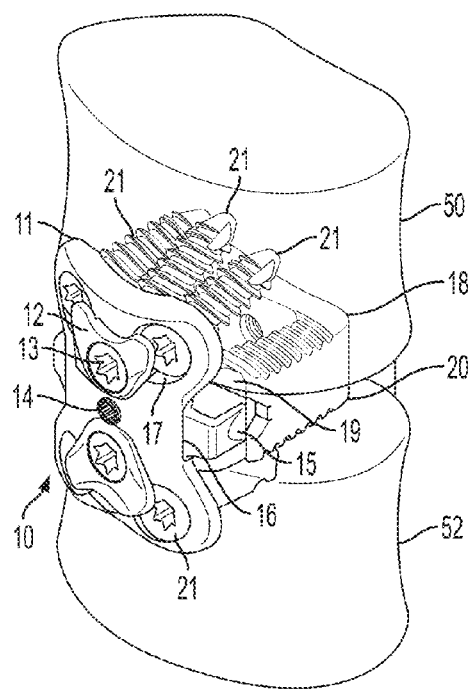
FIG. 3A and FIG. 3B show a perspective view and side view respectively of an exterior face plate device connected to an anterior cervical device located between adjacent vertebral bodies.
Figure 3B:
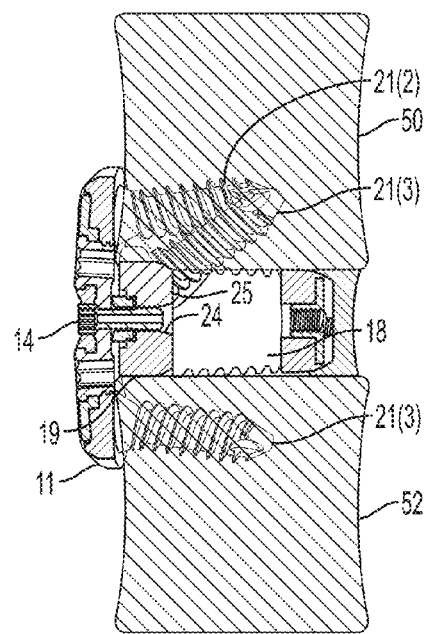

The interaction of the anterior placement of invention to the anterior cervical device is shown in FIG. 3A and FIG. 3B. FIG. 3A depicts how the alignment tabs 15 align with the anterior cervical device 20. The alignment tabs 15 center the exterior face plate 10 about the centerline of the anterior cervical device component 20 as well as establish a perpendicular condition. The alignment tabs 15 contact the face plate 19 in order to align the exterior face plate. The alignment tabs 15 include a notch or break away feature 16 on both sides of the anterior plate 11 at a point of contact of alignment tab 15 with the face plate 19. These notches or break away features 16 allow for easy separation of the tabs from the plate if it would be desired by the surgeon. When removed, the notches 16 will result in a smooth beveled edge on the plate 11.

FIG. 3A also shows the positioning of the bone screws 21 in the anterior plate 11 relative to the anterior cervical device 20. The bone screws 21 are inserted into the openings 17 in the anterior plate 11 and are screwed into vertebral bodies 50 and 52, as is seen in FIG. 3B.

FIG. 3B depicts the function of the threaded connector 14 or other connection means. The threaded connector 14 or other connection means mechanically joins the anterior plate 11 to the anterior cervical device 20 through a bore 23 in the anterior plate 11 that is aligned with a bore 24 in the face plate 19. This function may be used to pull the anterior plate up tight against the bone faces of the vertebral bodies and to add additional stability of the overall construct. The threaded connector or other connection means is self-captured to the anterior plate but may be removed and/or discarded if the surgeon does not want to incorporate this feature. This connector could be used prior to, or subsequent to, the placement of bone screws through the anterior plate.

FIG. 3B depicts the combination of the exterior face plate 10 and anterior cervical device 20 as would be seen when placed between vertebral bodies 50 and 52. Bone screws 21(1)-(3) are shown in functional locations. For example, bone screws 21(1) and 21(2) are each shown inserted through an opening 17 of the anterior plate 11, respectively. Bone screw 21(3) is shown inserted through a bore 25 of the face plate 19. The bone screw 21(3) permits the face plate 10 and the cage 18 to be secured to the vertebral body 50.

Referring to FIG. 3A, the anterior plate 11 incorporates an anti-back out mechanism 12 that keeps the bone screws 21 from backing out and/or away from the anterior plate. FIG. 1 and FIG. 2 depict the anti-back out plates 12 in a "pre-deployed" position. Once the bone screws 21 are in their desired locations, the anti-back out screw 3 is turned clockwise. The anti-back out plates 13 will rotate along with the screw 13 and nest into the opening 17, effectively blocking the path and ability of the bone screws (11) to back out of the plate. FIG. 3A depicts the anti-back out plates in their "deployed" position.

The device is depicted in a "Single Level Construct" bridging the gap between two vertebral bodies and filling the space of one disk. This is a simple depiction, so it should be understood that the device would be offered in numerous lengths for a single level construct, as well, it would be offered in varieties that would cover more than one level, i.e. 2 to 5 levels. For each additional level, the anterior plate would have another set of two bone screw holes and the appropriate anti-back out hardware. Additional constructs of the anterior cervical or similar device can be used at each level.

In the preceding detailed description, the invention is described with reference to specific exemplary embodiments thereof and locations of use within the spine. Various modifications and changes may be made thereto without departing from the broader spirit and scope of the invention as set forth in the claims. The specification and drawings are, accordingly, to be regarded in an illustrative rather than a restrictive sense.

What is claimed is:
1. A spinal fusion device, comprising:
   a U-shaped load bearing component and an anterior component, wherein the load bearing component and the anterior component are configured to mate to form at least one opening, wherein the anterior component includes a bore for receipt of a bone screw, and further wherein the anterior component includes a middle bore that transverses an anterior face of the anterior component and an opposing face of the anterior face;
   an external outer plate configured to span two vertebrae, wherein the external outer plate includes a plurality of bores configured to receive bone screws for coupling to a vertebra, and wherein the external outer plate includes a middle bore that aligns during use with the middle bore of the anterior component to receive an elongate fastener; and wherein the external outer plate has a low profile; and
   a pair of alignment tabs that extend from the external outer plate towards the anterior component, and wherein ends of the pair of alignment tabs are parallel to one another and have a width that corresponds to a width of the anterior component.

2. The spinal fusion device of claim 1, further comprising an anti-backout mechanism coupled to the external outer plate.

3. The spinal fusion device of claim 1, wherein the pair of alignment tabs comprise a break-away feature at a point of contact between the pair of alignment tabs and the external outer plate, which allows the pair of alignment tabs to be removed from the external outer plate.

4. The spinal fusion device of claim 1, wherein the pair of alignment tabs establish a perpendicular condition between the external outer plate and the anterior component when the external outer plate abuts the anterior component.

* * * * *